United States Patent [19]

Schafer

[11] Patent Number: 4,711,243
[45] Date of Patent: Dec. 8, 1987

[54] CORTICAL HEARING AID

[75] Inventor: Curtiss R. Schafer, Norfolk, Conn.

[73] Assignee: Cortronix, Inc., Newtown, Conn.

[21] Appl. No.: 890,027

[22] Filed: Jul. 28, 1986

[51] Int. Cl.[4] ............................................. A61N 1/30
[52] U.S. Cl. ................................. 128/420.5; 128/421; 128/420.6
[58] Field of Search ................ 128/1 R, 419 R, 421, 128/420 A, 420.5, 420.6, 1.6; 381/68, 68.2, 68.3, 68.4

[56] References Cited

U.S. PATENT DOCUMENTS

| | | | |
|---|---|---|---|
| 4,052,572 | 10/1972 | Schafer | 381/68.2 X |
| 4,167,189 | 9/1979 | Taihi et al. | 128/421 |
| 4,254,776 | 3/1981 | Tanie et al. | 128/421 |
| 4,495,384 | 1/1985 | Scott et al. | 381/68 X |
| 4,532,930 | 8/1985 | Crosby et al. | 128/421 X |
| 4,596,902 | 6/1986 | Gilman | 381/68 X |
| 4,606,329 | 8/1986 | Hough | 128/421 X |
| 4,617,536 | 10/1986 | Richard | 381/68 X |

*Primary Examiner*—Edward M. Coven
*Attorney, Agent, or Firm*—Lawrence Hager

[57] ABSTRACT

The cortical hearing aid is an instrument that produces the sensation of hearing by electrical stimulation of the neurons in the auditory cortex and/or auditory nerve trunk (eighth cranial nerve). The device employs an oscillator that generates a radio frequency carrier at a selected frequency within the range of 20 KHz to 60 KHz, with about 40 KHz producing optimum effectiveness. The RF carrier is modulated by the audio signal. An unbalanced bridge modulator is utilized to produce a modulated signal having substantially improved bandwidth and fidelity.

18 Claims, 11 Drawing Figures

CORTICAL HEARING AID

FIELD OF THE INVENTION

The invention relates to a system and circuitry for effecting so-called cortical hearing and, more particularly, to a circuit for improving bandwidth and/or fidelity of modulation of the carrier frequency.

BACKGROUND OF THE INVENTION

In recent years a great deal of interest has been shown in the provision of a means to enable the deaf to hear without use of their ears.

In my U.S. Pat. Nos. 4,052,572 issued Oct. 4, 1977 and 4,220,830 issued Sept. 2, 1980 there are disclosed two particular forms of hearing aid that I have called a "cortical hearing aid".

For best results with the profoundly deaf, the cortical hearing aid described in my U.S. Pat. No. 4,052,572 generally requires a radio frequency carrier of fixed frequency somewhere in the range between 30 KHz and 100 KHz. This carrier is amplitude modulated by the audio-frequency signals that convey the desired information to the deaf person.

As noted in my U.S. Pat. No. 4,220,830 a carrier signal may be modulated to produce a suppressed-carrier modulated signal. In a cortical hearing aid of this type, it is of great importance to use a carrier whose frequency is extremely low as compared to the amplitude modulated signals used in radio broadcast transmission. A balanced bridge modulator (14) is utilized. This is because the upper limit (e.g. 10 KHz) of the audio-frequency spectrum used as modulation approaches the lower range of the optimum carrier-frequency range. Thus, in accordance with my U.S. Pat. No. 4,052,572 the modulation frequency bandwidth is limited to approximately 7 KHz or lower to prevent distortion. This is because the capacitors used to stabilize the operation of the modulator shunts the higher audio frequencies to ground.

Other prior patents of interest include U.S. Pat. Nos. 2,373,569 issued 4/1945 to Kannenberg; 3,238,472 issued 3/1966 to Crompton-Couvela; 3,393,279 issued 7/1968 to Flanagan; 3,514,720 issued 5/1970 to Roucache et al; 3,811,098 issued 5/1974 to Williams; 4,052,572 issued 10/1977 to Schafer, and 2,703,344 issued 3/1955 to Anderson.

These patents are mentioned as being representative of the prior art and other pertinent references may exist. None of the above cited patents are deemed to affect the patentability of the present claimed invention.

The present invention involves a novel combination of features and circuitry combined in such a way as to afford a very efficient, cost effective, solution to the difficulties and problems encountered with the prior art.

The use of modulating frequencies as high as 20 KHz is desirable for most accurate discrimination of speech and the fullest enjoyment of music.

The present invention resides in part on the discovery that an unbalanced bridge amplitude modulator may be utilized in a cortical hearing aid to provide improved bandwidth (e.g. up to 20 KHz) of the modulated audio signal; generally eliminates sensitivity to destabilization with electrode length variation; eliminates any problem associated with input (audio) frequency doubling; improves uniformity of bandwidth at different proportions of modulation levels and appears to provide improved signal fidelity over an increased bandwidth range.

The Cortical Hearing Aid is a device designed to produce the sensation of hearing by electrical stimulation. Electroacoustic transducers or electrode implants (or any other form of surgery) are not required. The carrier (about 40 KHz) is modulated by the amplified output of a microphone or audio oscillator, and this modulated signal is applied to the patient through two electrodes: (1) a bare metal electrode (indifferent electrode) which is electrically at ground potential and may be placed anywhere on the patient's body; (2) the other is an insulated electrode (stimulus electrode) which is lightly held against the most effective area of the patient's head. This area must be determined by experiment, and does vary somewhat from patient to patient. The placement of the stimulus electrode determines the most effective "point of entry" for the signal.

In effect, the electronic circuitry scans the neurons at a rate of 40,000 times per second and thus is the electrical equivalent of several thousand electrodes. It operates on a constant current basis, so that current flow is largely independent of the electrical impedance of the patient's head. This frequency is high enough so there is no possibility of interference with "brain waves" (Alpha, 8 to 13 Hz; Beta, 14 to 30 Hz; Theta, 4 to 7 Hz; Delta, 0.5 to 3.5 Hz), or pacemaker (heart) pulses. At the same time, the 40 KHz frequency is low enough so that it is out of the range of those frequencies producing overheating of internal body organs (150 to 1250 mHz) or cataracts in the eyes (100 to 10,000 mHz).

SUMMARY OF THE INVENTION

A (cortical) hearing aid comprising:
a source of audio frequency signals;
means for providing a carrier frequency signal;
an unbalanced bridge modulator responsive to the audio frequency source and the carrier frequency signal to provide a modulated carrier frequency signal having substantially greater bandwidth; and
means including an electrode coupled to the modulator and adapted to be placed against a subject's head to couple the modulated signal into the subject.

Accordingly, it is an object of the present invention to provide a new and improved hearing aid.

Another object of the present invention is to provide an improved cortical hearing aid.

Another object of the present invention is to provide a cortical hearing aid having wider bandwidth.

Another object of the present invention is to provide a cortical hearing aid having an unbalanced bridge amplitude modulator.

Another object of the present invention is to provide a cortical type hearing aid which is less sensitive to destabilization.

Another object of the present invention is to provide a cortical type hearing aid which does not double the input audio frequency.

Another object of the present invention is to provide a hearing aid having substantially improved uniformity of bandwidth at different percentages of modulation.

Another object of the present invention is to provide a hearing aid having improved signal fidelity over an increased bandwidth range.

BRIEF DESCRIPTION OF THE DRAWINGS

Other objects and advantages of the present invention will be evident from the following detailed description when read in conjunction with the accompanying drawings which illustrate the preferred embodiment. Similar reference numerals refer to similar parts throughout.

DESCRIPTION OF THE PREFERRED EMBODIMENTS

Figure 1:
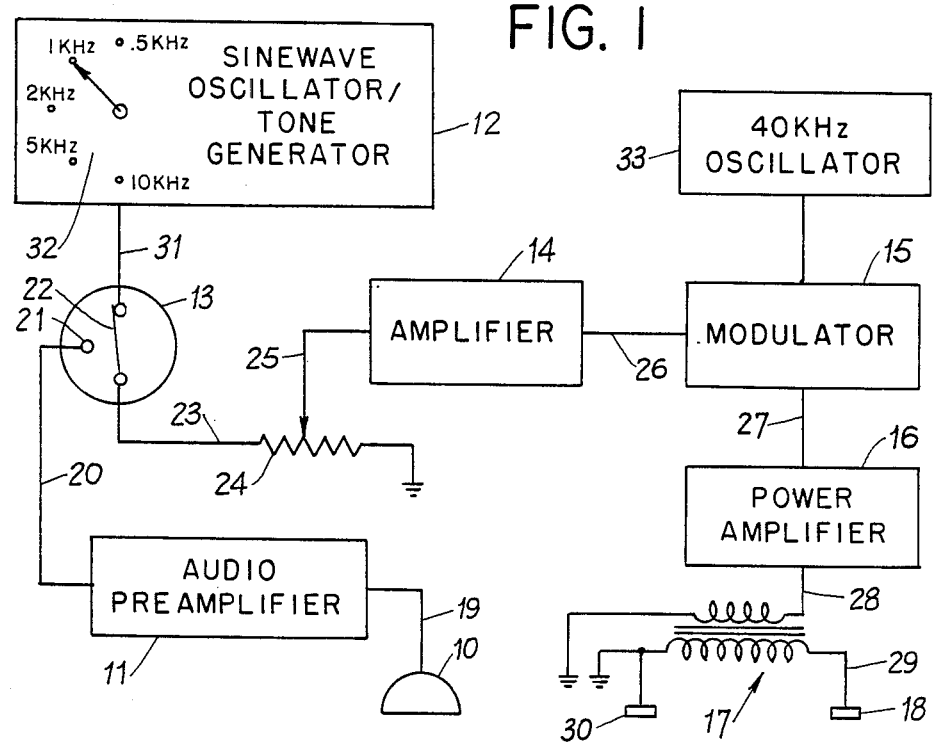
FIG. 1 is a schematic block diagram of a hearing aid in accordance with the present invention.

Referring to the drawings in general and to FIG. 1 in particular, shown therein is a cortical hearing aid in accordance with the preferred embodiment of the present invention. The cortical hearing aid generally includes a microphone 10, an audio preamplifier 11, a sinewave oscillator/tone generator 12, a select switch 13, an amplifier 14, an amplitude modulator 15, a power amplifier 16, an output transformer 17, and electrodes 18, 30.

Microphone 10 may be of conventional design. Microphone 10 is generally used to convert speech, music and other sounds into electrical (audio) signals in the range 0 to 20 KHz. These electrical audio signals are coupled, via lead 19, to the input of audio preamplifier 11.

Audio preamplifier 11 may be of conventional design to effec amplification of the electrical (audio) signal. The amplified electrical (audio frequency) signal is coupled, via lead 20, to switch contact 21 of select switch 13. With wiper 22 switched to contact 21 as shown in phantom outline, the electrical (audio) signal is coupled, via lead 23, to potentiometer 24 and the input of amplifier 14.

Potentiometer 24 may be of conventional design. The function of potentiometer 24 is to vary the intensity of the electrical (audio) signal input to the amplifier 14. Potentiometer wiper 25 may be selectively adjusted to effect modulation from 0 to 100%.

Amplifier 14 may be of conventional design to effect the desired amplification of the electrical (audio frequency) signal. The output of amplifier 14 is coupled, via lead 26, to the modulation input of modulator 15.

Modulator 15 provides amplitude modulation to a carrier signal of approximately 40 KHz. The amplitude modulation coincides with the electrical (audio frequency) signal. Modulator 15 will be discussed in greater detail hereinafter with reference to FIG. 2. The output of modulator 15 is coupled, via lead 27, to the input of power amplifier 16.

Power amplifier 16 may be of conventional design with its output coupled, via lead 28, to transformer 17.

Transformer 17 may be of conventional design to effect a voltage step-up across its secondary winding, with the signal output coupled, via lead 29, to electrodes 18, 30.

Electrode 18 is a metal disc that is covered with a thin layer of TEFLON insulation to provide an impedance that makes the device essentially a constant-current source and thus largely independent of the electrical properties of the patient's head. In an example it is a disc of about one-inch diameter. It is placed against the user's head at a place chosen by the user for optimum effect, usually at a spot forward and above the ear canal and to the rear of the temple. Electrode 30 which is not insulated may be of any size and proportion and connected to the user at any place, as at the hand.

With switch 13 having its wiper 22 connected or switched as shown in solid line, audio preamplifier 11 is disconnected from modulator 15. And sinewave oscillator/tone generator 12 is connected, via lead 31 and switch 13 and potentiometer 24 and amplifier 14, to modulator 15.

Sinewave oscillator 12 may be of conventional design having switch means 32 to enable selection of a plurality of different frequencies, e.g., 500 Hz, 1 KHz, 2 KHz, 5 KHz, 10 KHz, test signals for modulating the 40 KHz carrier signal produced by modulator 15. Sinewave oscillator 12 is provided for test purposes to give fixed reference points to enable comparison studies between different patients.

Figure 2:
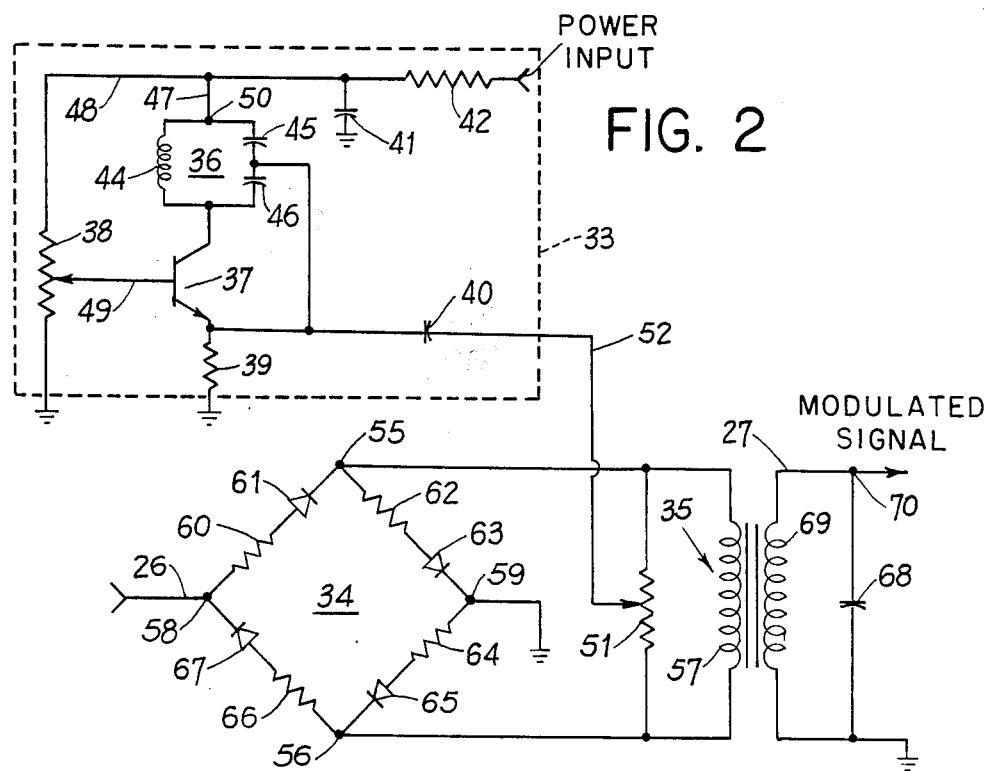
FIG. 2 is a circuit diagram of the modulator in accordance with the present invention.

With particular reference to FIG. 2, modulator 15 will now be described in more detail.

Basically speaking, modulator 15 comprises an unbalanced bridge network 34 and a transformer 35.

Sinewave oscillator 33 utilizes an LC network 36, transistor 37, potentiometer 38, a bias resistor 39 and coupling capacitor 40. Capacitor 41 and resistor 42 serve to filter and isolate the power input on lead 43 from a conventional power source (not shown). LC network 36 generally comprises a 40 millihenry inductor 44 and a pair of 0.02 microfarad capacitors 45 and 46. The top of LC network, i.e., junction 50, is connected, via leads 47 and 48 to the top of potentiometer 38 to form a feedback path. Potentiometer 38 has its low end connected to ground and its wiper arm 49 connected to the base of transistor 37. Potentiometer 38 is approximately a 10 K-ohm device which functions as a biasing resistor for obtaining the proper bias on transistor 37. The collector of transistor 37 is connected to the junction between inductor 44 and capacitor 46. The emitter of transistor 37 is connected to the junction of capacitors 40, 45, 46, and resistor 39. Resistor 39 serves to develop the output voltage sinewave signal which is coupled across capacitor 40 to potentiometer 51, via lead 52. Capacitor 40 is a 0.01 microfarard capacitor which serves as a DC blocking and alternating signal coupling capacitor.

Unbalanced bridge network 34 has its output terminal points 55 and 56 connected across potentiometer 51 and the primary 57 of transformer 35. The electrical (audio frequency) signal output from microphone 10 or the test signal output from sinewave oscillator/tone generator 12, via lead 26, is coupled to bridge junction point 58. Bridge network junction point 59 is connected to circuit ground. Each leg of the unbalanced bridge network 34 comprises a resistor and a diode. Accordingly, resistor 60 and diode 61 are connected in series between junction points 58 and 55, with diode 61 being forward biased in the direction of junction point 55. Resistor 62 and diode 63 are connected in series between junction points 55 and 59, with diode 63 being forward biased in the direction of junction point 59. Resistor 64 and diode 65 are connected in series between junction points 59 and 56, with diode 65 being forward biased in the direction of junction point 56. Resistor 66 and diode 67 are connected in series between junction points 56 and 58, with diode 67 being forward biased in the direction of junction point 58. Capacitor 68 is connected across the secondary winding 69 of transformer 35. Capacitor 68 functions as a tuning capacitor. The modulated signal output developed at junction point 70 is coupled, via lead 27, to power amplifier 16, transformer 17 and probe 18.

Figure 3:
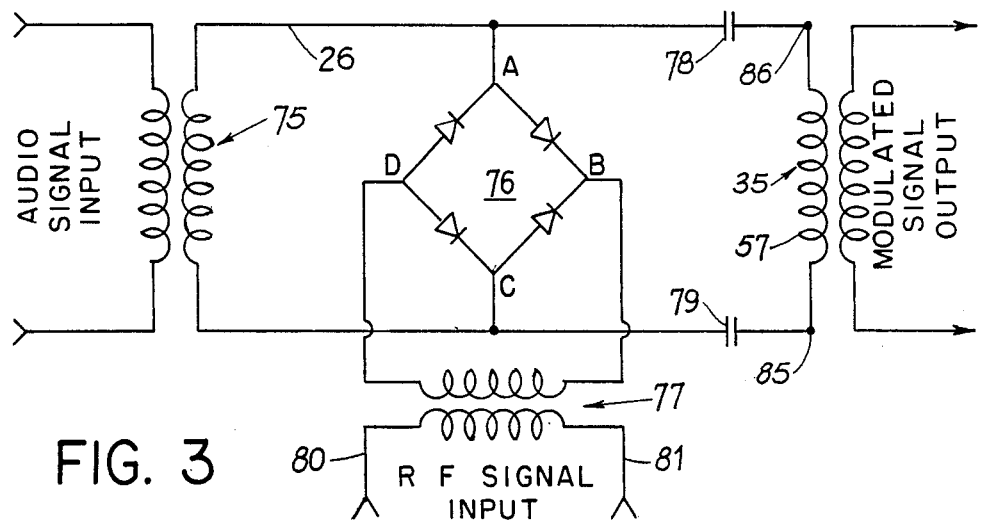
FIG. 3 is a circuit diagram of an alternative embodiment of a portion of the modulator as shown in FIG. 2.

With reference now to FIG. 3, another embodiment of the modulator shown in FIG. 1 according to the invention is illustrated. With the exception of the alternative modulator circuitry, the operation and other details of the modulator 15 remain basically the same. In accordance with this alternative embodiment, the audio signal is coupled via transformer 75 across terminals A and C of bridge 76. The RF carrier signal is coupled via transformer 77 across terminals B and D of bridge 76. The modulated signal is coupled via capacitors 78 and 79 across the primary 57 of transformer 35. Transformer primary leads 80 and 81 are coupled to leads 52 and ground of 40KHz oscillator 33.

Figure 4:
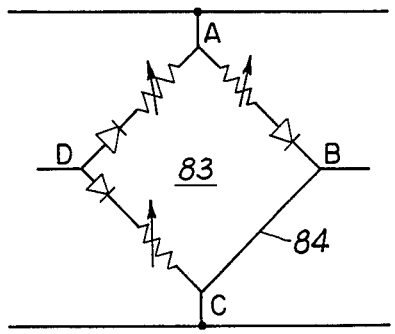
FIG. 4 is a circuit diagram of another alternative embodiment of the unbalanced bridge network.

With reference now to FIG. 4, the bridge network shown at 76 in FIG. 3 is unbalanced by shorting out one leg of the bridge, or by making capacitor 78 much larger (in electrical value) than capacitor 79.

Figure 5:
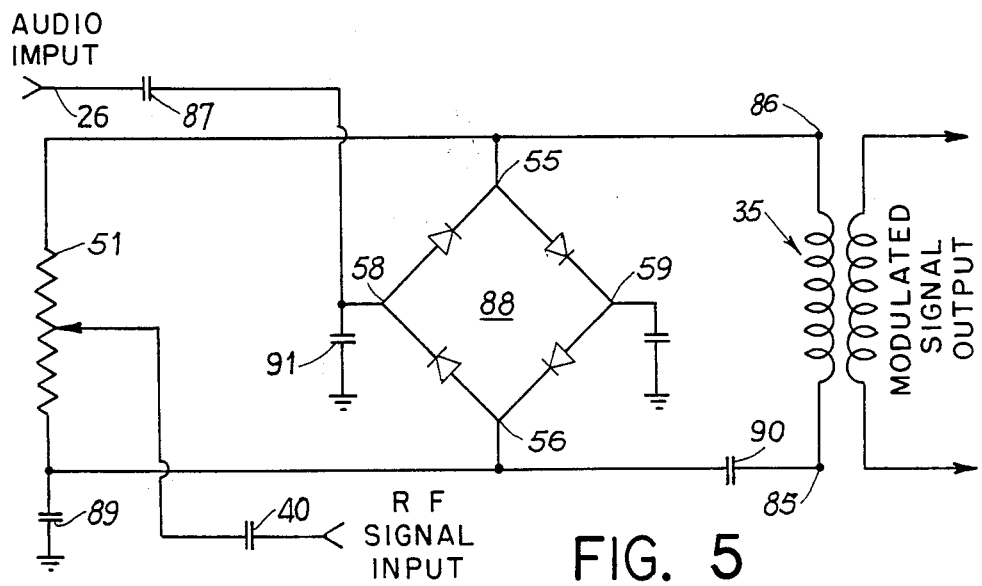
FIG. 5 is a circuit diagram of another alternative embodiment of the unbalanced bridge network.

With reference now to FIG. 5, another alternative embodiment of modulator 15 is shown. With the exception of the illustrated unbalanced bridge network, the operation and other details of the modulator 15 remain basically the same. In this embodiment, the audio signal, via lead 26 and capacitor 87, is coupled to terminal 58 of unbalanced bridge 88. The RF carrier signal (not shown) is coupled, via lead capacitor 40, to potentiometer 51 in similar manner as described above with reference to FIG. 2. Unbalanced bridge 88 is similar to unbalanced bridge 34, except that series resistors 60, 62, 64 and 66 have been eliminated. Capacitors 89, 90, and 91 basically serve as DC blocking capacitors.

Figure 6:
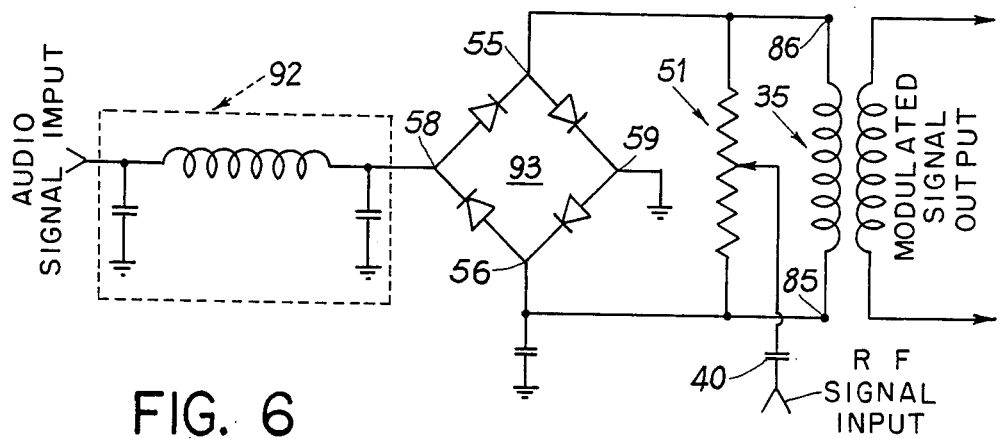
FIG. 6 is a circuit diagram of another alternative embodiment of the unbalance bridge network.

With reference now to FIG. 6, yet another alternative embodiment of modulator 15 is shown. With the exception of the illustrated unbalance bridge network, the operation and other details of modulator 15 remain basically the same. In this embodiment, the audio signal (not shown) is coupled via filter network 92 to terminal 58 of unbalanced bridge 93.

Figure 7:
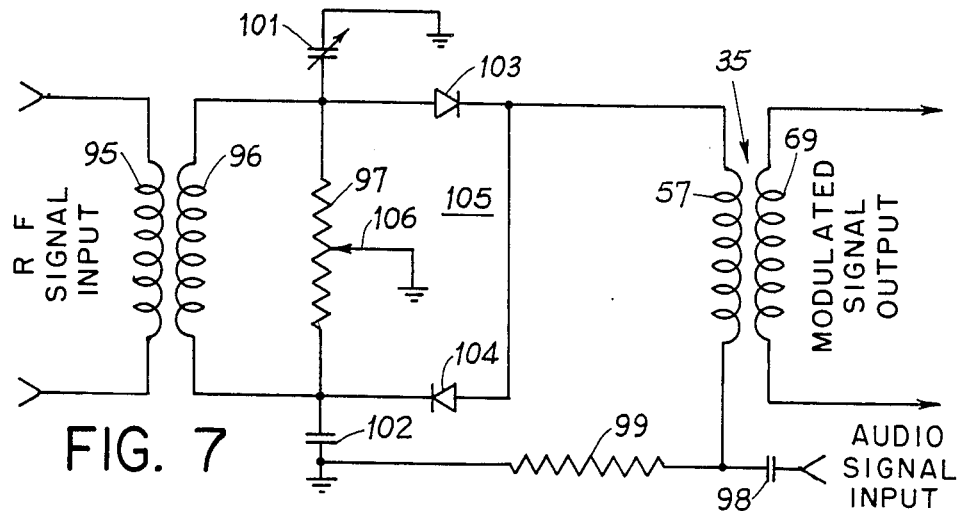
FIG. 7 is a circuit diagram of another alternative embodiment of the unbalanced bridge network.

With reference now to FIG. 7, yet another alternative embodiment of modulator 15 is shown. In this embodiment, the RF signal (not shown) is coupled from transformer primary 95 to transformer secondary 96 and across potentiometer 97. The audio signal (not shown) is coupled via capacitor 98 across resistor 99. Thus, the audio signal is developed across resistor 99, which effects modulation across transformer primary 57. Capacitors 101 and 102 affect stability, D.C. blocking and high frequency rejection. Diodes 103 and 104 each form one leg of the unbalanced bridge network 105. The other two legs of unbalanced bridge network 105 are effected by the wiper 106 of potentiometer 97.

The position of wiper 106 may be selected to effect a desired unbalancing of the RF signal which is modulated by the audio signal as noted above. The modulated signal is then coupled to the secondary winding 69 of transformer 35. The remaining operation and other details of modulator 15 remain basically the same.

It must be remembered that optimum bridge unbalance is to be produced only by setting potentiometer 51 in FIGS. 5 and 6, and potentiometer 97 in FIG. 7, at the setting which produces zero or minimum frequency doubling of the audio input signal.

Figure 8:
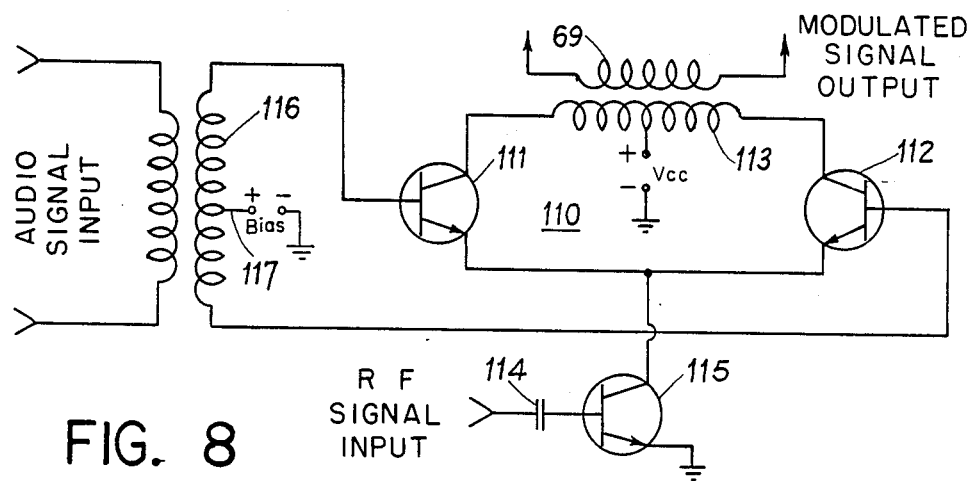
FIG. 8 is a circuit diagram of another alternative embodiment of the unbalanced bridge network.

With reference now to FIG. 8, another embodiment of the modulator shown in FIG. 2 is illustrated. With the exception of the alternative modulator circuitry, the operation and other details of modulator 15 remain basically the same. In this embodiment, the unbalanced bridge network 110 is formed by transistors 111 and 112, and by a center tap transformer 113. Each transistor 111 and 112 forms a leg of the unbalanced bridge network 110. Each half of transformer 113 forms a leg of unbalanced bridge network 110. Capacitor 114 and transistor 115 couple the RF signal into bridge network 110. The audio signal (not shown) is coupled via transformer 116 to the base elements of transistors 111 and 112. Bias tap 117 is selected to effect a desired unbalance condition to transistors 111 and 112, which cause bridge network 110 to operate in an unbalanced state. The audio signal modulated RF is coupled via center tap transformer 113 primary to its secondary winding 69.

Figure 9:
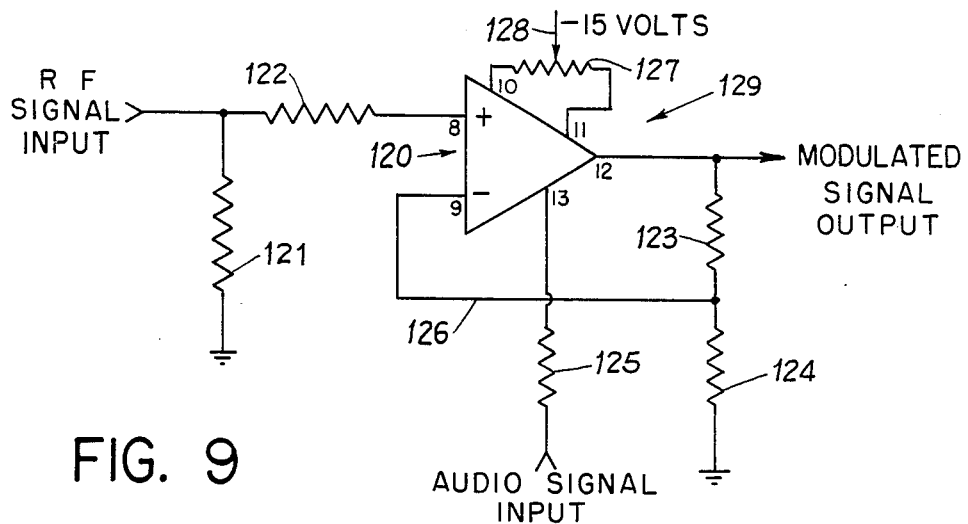
FIG. 9 is a circuit diagram of another alternative form of the modulator using an operational amplifier.

With reference now to FIG. 9, another alternative embodiment of the modulator shown in FIG. 2 is illustrated. The RF signal (not shown) is coupled via resistor 121 and 122 to the (+) input of op-amp 120. Resistor 123 and resistor 124 set the direct current operating point for the amplifer; resistor 125 couples the audio signal unto pin 13 of op-amp 120. Potentiometer 127 is the offset voltage adjustment.

The circuit of FIG. 9 does not frequency double; it is an amplitude modulator in which modulation is accomplished by varying the gain of one side of the differential amplifier (that constitutes the operational amplifier) with the introduction of the audio signal.

Figure 10A:
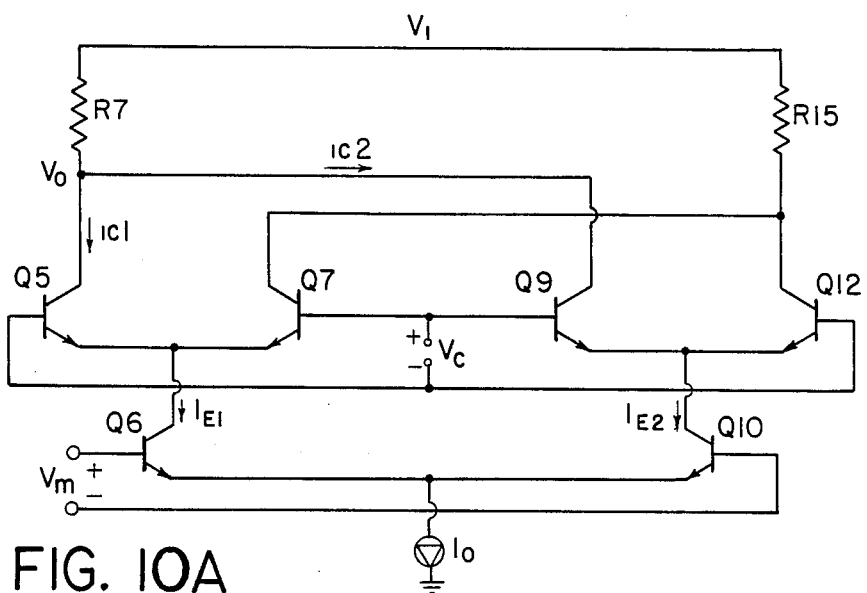
FIGS. 10A and 10B are circuit diagrams of a four-quadrant multiplier used as a modulator.
Figure 10B:
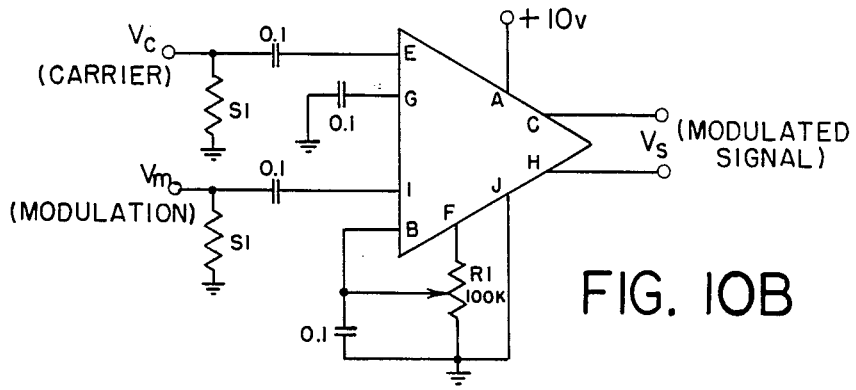

FIG. 10A shows a four quadrant multiplier which, applicant discovered, makes an excellent amplitude modulator for use in the cortical hearing aid in accordance with the invention. This multiplier consists of two cross-coupled differential amplifiers which are jointly controlled by a third differential amplifer. The carrier frequency is fed in at Vc and the modulating frequency as Vm. The complete circuitry is shown in FIG. 10B. The balance adjustment R1, in accordance with the invention, is changed to effect an unbalanced operation, whereby the input audio frequency is, as discovered by applicant, the same as the modulated output frequency.

While certain specific embodiments have been set forth for the invention for the sake of illustration to persons skilled in the art, it is not intended to be limitative. Consequently, the invention should be construed broadly in accordance with its full spirit and scope.

What is claimed is:
1. A hearing aid comprising:
a microphone means (10) for detecting sound and producing an audio frequency signal representative of the detected sound;
a sinewave oscillator/tone generator means (12) for producing an audio frequency test signal;
variable resistance means (24);

switch means (13) operatively connected for selectively coupling said audio frequency signal and said audio frequency test signal to said variable resistance means;

amplifier means (14) operatively coupled to said variable resistance means for amplifying said audio frequency signal and said audio frequency test signal;

amplitude modulator means (15) including an unbalanced bridge rectifier (34) operatively coupled to said amplifier means, and including a carrier frequency generator means (33) for producing a carrier frequency in the range of about 40 KHz, and including a first transformer means (35) operatively coupled to said carrier frequency generator means and to said unbalanced bridge rectifier for producing a composite signal;

power amplifier means (16) operatively coupled to said amplitude modulator means and being responsive to said composite signal for producing an amplifier composite signal;

second transformer means (17) operatively coupled to said power amplifier and being responsive to said composite signal for producing a stepped-up voltage signal representative of said amplified composite signal;

probe means (18, 30) responsive to said voltage signal for producing a probe signal representative of said voltage signal and for impressing said probe signal on the person of the user.

2. A hearing aid as in claim 1, wherein:
the carrier frequency generator is a colpitts oscillator.

3. A cortical hearing aid, for a hearing impaired user, comprising:

means (10) for detecting a sound and producing an audio frequency signal representative thereof;

modulator means (15) having an unbalanced bridge rectifier (34), a carrier frequency generator (33), a potentiometer (51), and a first transformer (35), said unbalanced bridge rectifier includes a first rectifier (61) with an anode connected to a first terminal (55) and a cathode connected to a second terminal (58) and having a second rectifier (67) with an anode connected to said second terminal and a cathode connected to a third terminal (56) and having a third rectifier (63) with an anode connected to a fourth terminal (59) and a cathode connected to said first terminal, said first transformer having a primary (57) operatively coupled across said first and third terminals, said potentiometer (51) being operatively coupled across said first and third terminals with a wiper terminal operatively coupled to said carrier frequency generator, said second and fourth terminals being operatively coupled to said means (10) for producing said audio frequency signal, said modulator means being responsive to a carrier frequency and said audio frequency signal for producing a modulated signal;

means (16,17,18,30) responsive to said modulated signal for impressing a corresponding output signal on the person of the user.

4. A hearing aid having particular utility for a profoundly deaf person, comprising:

means for detecting sound and providing an electrical audio frequency signal representative of the detected sound;

means for providing a carrier frequency;

an unbalanced mdulator means operatively coupled to said detecting means and being responsive to said electrical audio frequency signal and operatively coupled to said means for providing a carrier frequency and being responsive to said carrier frequency for providing a modulated carrier signal; and means operatively coupled to said unbalanced modulator means and being responsive to said modulated carrier signal for impressing the modulated carrier signal on the person of the user.

5. A hearing aid as in claim 4, wherein:
the unbalanced modulator has a modulation bandwidth range between 10 Hz to 20 KHz.

6. A hearing aid as in claim 4, wherein
the carrier frequency is in the range of about 30 KHz to 60 KHz.

7. A hearing aid as in claim 4, wherein:
the carrier frequency is approximately 40 KHz; and
the modulating electrical audio frequency signal is in the range of about 10 Hz to 20 KHz.

8. A hearing aid as in claim 4, including:
a source of audio test signals representing a spectrum of the sounds to be heard; and
switch means for selectively coupling said audio test signals and said electrical audio frequency signals to said unbalanced modulator means.

9. A hearing aid as in claim: 1, wherein:
the unbalanced modulator includes a bridge rectifier(34) having a first rectifier (61) with an anode connected to a first terminal (55) and a cathode connected to a second terminal (58), and having a second rectifier (67) with an anode connected to said second terminal and a cathode connected to a third terminal (56), and having a third rectifier (63) with an anode connected to a fourth terminal (59) and a cathode connected to said first terminal, and having a transformer (35) with a primary winding (57) connected across said first and third terminals, and having a potentiometer (51) connected across said first and third terminals with wiper terminal connected to said means for providing a carrier frequency, said second and fourth terminals being operatively coupled to said means providing said electrical audio frequency signal.

10. A hearing aid as in claim 4, wherein:
the means for detecting sound includes a microphone.

11. A hearing aid as in claim 4, wherein:
the unbalanced modulator includes a bridge rectifier (76) having a first terminal (A) and a second terminal (B) and a third terminal (C) and a fourth terminal (D), and having a first transformer with its secondary winding (75) coupled across said first and third terminals, and having a second transformer (77) with its secondary winding coupled across said second and fourth terminals, and having a third transformer (35) including a primary winding and a secondary winding, and having a first capacitor (78) connected in series between said first terminal (A) and a first transformer terminal (86) of said third transformer, and having a second capacitor (79) connected in series between said third terminal (C) and a second transformer terminal (85) of said third transformer.

12. A hearing aid as in claim 4, wherein:
the unbalanced modulator includes a bridge rectifier (83) having a first (A) and a second (B) and a third (C) and a fourth (D) terminals, and having a first diode and a first variable resistor connected in series between said first and fourth terminals; and having a second diode and a second variable resistor connected in series between said first and said second terminals, and having a third diode and a third variable resistor connected in series between said third and said fourth terminals.

13. A hearing aid as in claim 4, wherein:

the unbalanced modulator includes a bridge rectifier (88) having a first terminal (58) connected to an audio signal input capacitor (87), and having a potentiometer (51) connected across a second (55) and a third (56) terminals of said bridge rectifier with a wiper terminal being connected to an RF signal input capacitor (40), and having a transformer (35) with its primary winding connected between a first circuit terminal (85) and a second circuit terminal (86), said first circuit terminal being connected to a first side of a capacitor (90), said capacitor (90) having a second side connected to said third terminal (56), said second circuit terminal (86) being connected to said second terminal (55).

14. A hearing aid as in claim 4, wherein:

the unbalanced modulator includes a bridge rectifier (93) having a first (55) and a second (56) and a third (58) and a fourth (59) terminals, and having an LC filter (92) connected to said third terminal, and having a potentiometer (51) connected across said first and second terminals with wiper arm connected to an RF signal input capacitor (40), and having a transformer (35) with a primary winding connected across said first and second terminals, said fourth terminal (59) being connected to a circuit ground.

15. A hearing aid as in claim 4, wherein:

the unbalanced modulator includes a bridge rectifier network (105) having a potentiometer (106) and an inductance means (96) and a pair of diodes (103, 104), and having a variable capacitor (101) connected between a circuit ground and to a first circuit junction between said inductance means (96) and said potentiometer (97) and one of said pair of diodes (103), and having a second capacitor (102) connected to a second circuit junction between said inductance means (96) and said potentiometer (97) and the other of said pair of diodes (104) and to one end of a resistor (99), and having a transformer (35) with a secondary winding (57) connected between a junction between said pair of diodes (103, 104) and to the other side of said resistor (99).

16. A hearing aid as in claim 4, wherein:

the unbalanced modulator includes a bridge rectifier network (110) comprising a secondary center tap winding of a first transformer (69) and a pair of transistors (111,112) and a secondary winding of a second transformer (116) having a first end connected to the base of one of said pair of transistors (111) and a second end connected to the base of the other of said pair of transistors(112).

17. A hearing aid as in claim 4, wherein:

the unbalanced modulator includes an operational amplifier (120) and circuit means (123, 124, 126, 127) for affecting an unbalanced bridge network audio signal modulation of a carrier signal.

18. A hearing aid as in claim 4, wherein:

the unbalanced modulator includes a four quadrant multiplier like circuit (150) having means (R1) for effecting an unbalanced operation of said four quadrant multiplier like circuit such that it effects an unbalanced modulation for producing said modulated carrier signal.

* * * * *